（12）United States Patent
France

(10) Patent No.: US 7,982,470 B2
(45) Date of Patent: Jul. 19, 2011

(54) MICROWAVE PROBE DEVICE

(75) Inventor: Garry George France, Queensland (AU)

(73) Assignee: Callidan Instruments Pty. Ltd., Queensland (AU)

( * ) Notice: Subject to any disclaimer, the term of this patent is extended or adjusted under 35 U.S.C. 154(b) by 438 days.

(21) Appl. No.: 12/300,048

(22) PCT Filed: May 10, 2007

(86) PCT No.: PCT/AU2007/000632
§ 371 (c)(1),
(2), (4) Date: Nov. 7, 2008

(87) PCT Pub. No.: WO2007/131268
PCT Pub. Date: Nov. 22, 2007

(65) Prior Publication Data
US 2009/0195259 A1    Aug. 6, 2009

(30) Foreign Application Priority Data

May 17, 2006  (AU) ............................... 2006902650
Jan. 30, 2007  (AU) ............................... 2007900430

(51) Int. Cl.
*G01N 22/00*    (2006.01)
(52) U.S. Cl. ........................... 324/639; 324/71.1

(58) Field of Classification Search ........... 324/637–643
See application file for complete search history.

(56) References Cited

U.S. PATENT DOCUMENTS

| 4,544,880 | A | * | 10/1985 | Nagy et al. .................... 324/642 |
| 4,788,853 | A |   | 12/1988 | Bell |
| 4,904,928 | A | * | 2/1990 | Lewis .......................... 324/636 |
| 2004/0100280 | A1 |   | 5/2004 | Ju et al. |
| 2005/0016683 | A1 |   | 1/2005 | Kim et al. |
| 2006/0061371 | A1 |   | 3/2006 | Inoue et al. |
| 2007/0203480 | A1 | * | 8/2007 | Mody et al. ................... 606/33 |

FOREIGN PATENT DOCUMENTS

| JP | 2004-101521 | 4/2004 |
| WO | WO 91/02966 A1 | 3/1991 |
| WO | WO 03/016887 | 2/2003 |
| WO | WO 2006/030060 A1 | 3/2006 |

* cited by examiner

*Primary Examiner* — Vincent Q Nguyen
(74) *Attorney, Agent, or Firm* — Hunton & Williams LLP

(57) ABSTRACT

A probe for obtaining a measure of one or more properties in a sample wherein the probe including a support member (2), a transmit antenna (4), a receive antenna (5) and a signal barrier (6). The signal barrier (6) is located between the transmit antenna (4) and the receive antenna (5) in order to force signals traveling between transmit antenna (4) and receive antenna (5) to propagate into the surrounding region. Modification of the microwave signal after it passes through the surrounding region is measured and used to infer one or more properties of the test material.

26 Claims, 6 Drawing Sheets

MICROWAVE PROBE DEVICE

FIELD OF THE INVENTION

This invention relates to a probe useful with a source of microwave signals to determine an amount of a component in a sample. In particular, the invention relates to a microwave probe that can be used to determine an amount of a component in a sample by measuring the change in a microwave signal after transmission through the sample. The invention is suitable for determining the amount of a component in a sample when the probe is immersed into a bulk amount of material.

BACKGROUND OF THE INVENTION

Measurement of the properties of materials is traditionally carried out using conventional laboratory analysis of a manually collected sample. This process is expensive and time consuming, and results for different material batches may be easily confused due to the time taken between sampling and the receiving of results. A device capable of delivering immediate results to the operator whilst in contact with the sample removes a large portion of potential errors and allows immediate decision making regarding the quality of said material due to its properties.

When a microwave signal passes through the material, some of the signal is absorbed such that the amplitude (i.e. power level) of the received microwave signal is less than was transmitted. The amount of attenuation may be directly related to the material property that is desired to be measured. In addition to monitoring attenuation, the velocity of the microwave signal is also affected by its passage through the material. This slowing of microwave velocity creates a phase shift in microwave signal. A phase shift is time difference between when a signal is received compared to when it should have been received with no interference. Attenuation and phase shift may be used to infer a number of compositional properties about the material being analysed.

GB 2,122,741 describes an apparatus for monitoring crushed coal. The apparatus monitors ash content and moisture content of the coal by respectively transmitting and detecting X-ray and microwave radiation. The microwave radiation amplitude is chopped at a low frequency of about 1.0 kHz, which is suitable for analysing a crushed sample such as coal. This apparatus, however, is not well suited for determining moisture content of other types of samples and is not easily portable.

U.S. Pat. No. 4,788,853 describes a moisture meter that also uses microwave signals at discrete discontinuous frequencies. This patent states that the number of frequencies required to perform the invention is not critical as long as sufficient data is generated. The device is designed for use with material moving on a conveyor belt.

AU 61689/90 describes an apparatus for determining moisture content in a sample of varying thickness on a conveyor belt. The microwave signals are also transmitted at discrete discontinuous frequencies within a selected range.

Although the above described apparatus may be useful for determining moisture content in a sample on a conveyor belt, these apparatus are nevertheless still prone to substantial errors or inaccuracies due at least in part to variation in sample depth or configuration. Furthermore the devices are not portable and therefore have limited usefulness.

In this specification, the terms "comprises", "comprising" or similar terms are intended to mean a non-exclusive inclusion, such that a method, system or apparatus that comprises a list of elements does not include those elements solely, but may well include other elements not listed.

OBJECT OF THE INVENTION

It is an object of the invention to provide an alternative or improvement to the abovementioned prior art.

SUMMARY OF THE INVENTION

In one form, though it need not be the only or indeed the broadest form, the invention resides in a probe comprising:
a support member;
a transmit antenna disposed towards an end of the support member;
a receive antenna disposed adjacent the transmit antenna; and
a signal barrier disposed on the support member between the transmit antenna and the receive antenna so as to force signals traveling from the transmit antenna to the receive antenna to propagate through a surrounding region.

In a further form the invention resides in a sample analysis device comprising:
a probe including a transmit antenna disposed towards an end of a support member;
a receive antenna disposed adjacent the transmit antenna;
a signal barrier disposed on the support member between the transmit antenna and the receive antenna so as to force signals traveling from the transmit antenna to the receive antenna to propagate through a surrounding region;
a source of signals connected to the transmit antenna; and
a signal processor connected to the receive antenna.

Further features of the present invention will become apparent from the following detailed description.

BRIEF DESCRIPTION OF THE DRAWINGS

In order that the invention may be readily understood and put into practical effect, preferred embodiments will now be described by way of example with reference to the accompanying figures wherein like reference numerals refer to like parts and wherein.

DETAILED DESCRIPTION OF THE INVENTION

Figure 1:
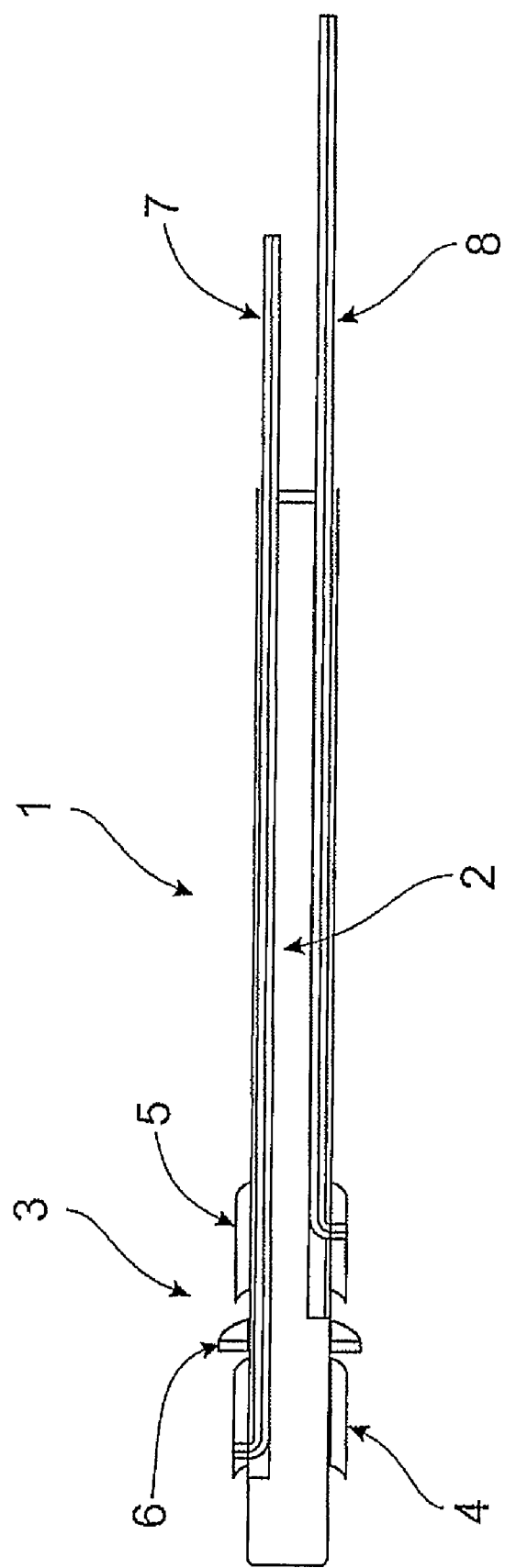
FIG. 1 is a sectional side view of a first embodiment of a probe.

Referring to FIG. 1, there is shown a schematic of a probe 1 consisting of a support member 2 with an antenna arrangement 3 towards one end. The antenna arrangement 3 comprises a transmit antenna 4 and a receive antenna 5 separated by a barrier 6. In one embodiment, the transmit antenna 4 is a brass cylinder affixed near the end of the support member 2. The receive antenna 5 is also a brass cylinder adjacent to the transmit antenna 4 but separated from the transmit antenna 4 by a barrier 6 composed of, for example, brass and/or microwave absorbing rubber.

In the preferred embodiment microwave signals are carried to the transmit antenna 4 by coaxial cable 7. The microwave signals emanate from the antenna 4 into surrounding material. After passing through the surrounding material, the microwave signals are received by the receive antenna 5 and carried by coaxial cable 8 for signal processing. The coaxial cables 7, 8 are suitably seated in grooves formed along the length of the support member 2.

Although the probe is described in terms of measurement using microwave signals it will be appreciated that the invention need not be limited to the specific frequency range. The inventor envisages that there may be applications where shorter or longer wavelength signals may be suitable.

Figure 2:
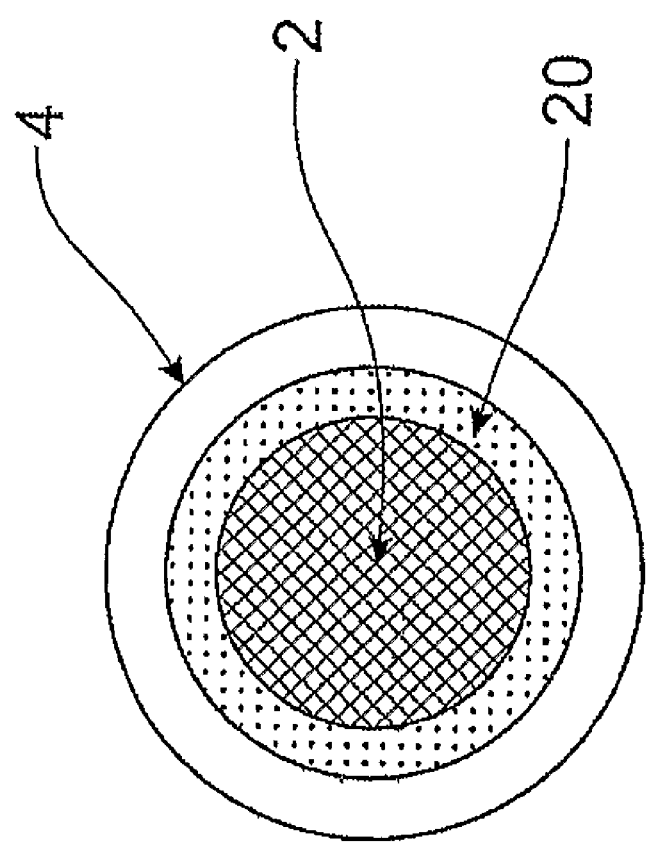
FIG. 2 is an end view of the probe of FIG. 1.

The support member 2 is formed of any suitable material. In one embodiment the support member is formed as a rod of a stiff material such as brass, in which case insulation material 20 (see FIG. 2) is located between the support member 2 and the antennas. The insulation material is formed of any suitable material which does not conduct signals, such as plastic or ceramic. If the support member 2 is formed from a material which itself does not conduct microwave signals, eg Teflon, the insulation material 20 is not required and may be omitted. Although a stiff support rod is preferred there may be applications where a flexible rod is more appropriate.

The transmit antenna 4 and the receive antenna 5 may be manufactured from any material capable of conducting microwave signals, such as brass or copper. The respective positions of the transmitting and receiving antennae are interchangeable, provided they are separated by barrier 6.

The barrier 6 may be manufactured from any material capable of blocking direct signal transmission between the transmit antenna 4 and the receive antenna 5. In one embodiment, the barrier is formed from brass and microwave absorbing rubber. The barrier may also be formed from an insulating ceramic material or plastic. In this case the barrier may be formed integrally with the support member 2.

Figure 3:
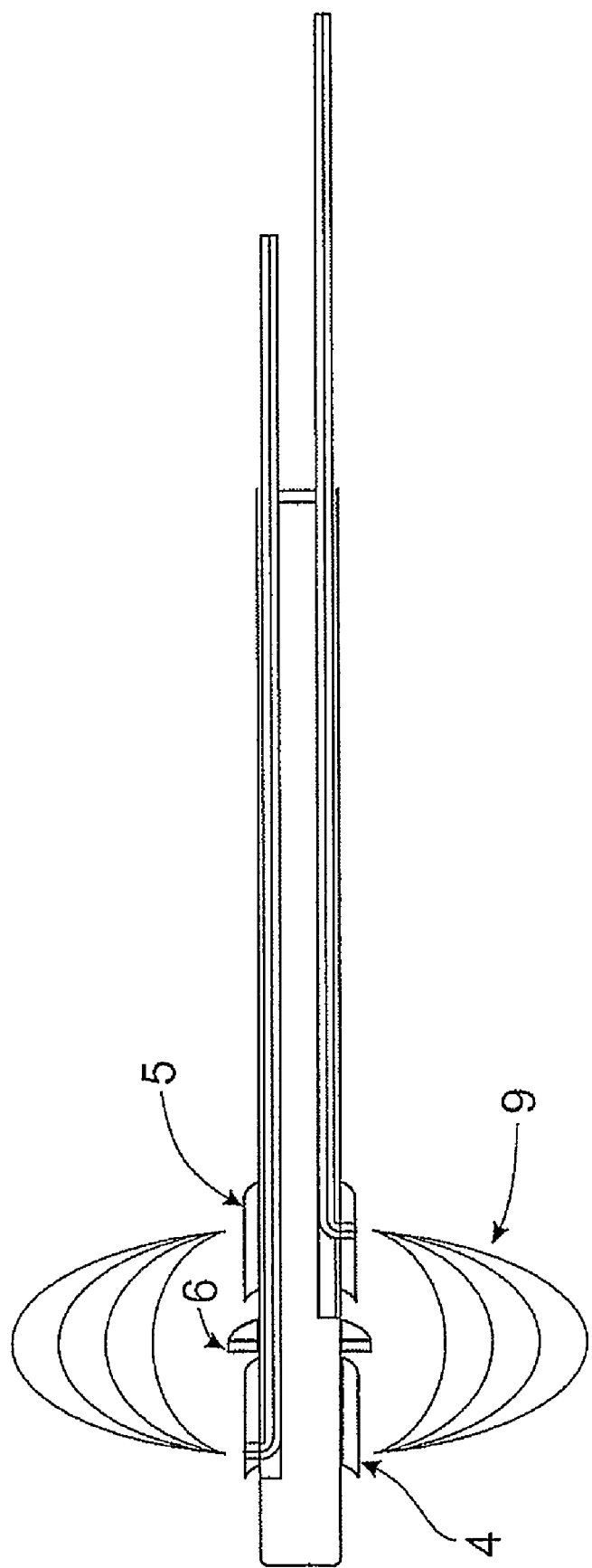
FIG. 3 is a side view of the probe of FIG. 1 during operation.

A microwave field generated by the probe 1 during operation is shown in FIG. 3. Microwave signals emanating from the transmit antenna 4 and received by the receive antenna 5 form a toroidal microwave field geometry 9. This field is formed because the barrier 6 prevents a direct path between the transmit antenna and the receive antenna. When the probe is inserted into a test material, the expanded microwave field is forced to traverse and interact with the surrounding material. The resulting signal attenuation and phase shift of the received microwave signal is processed and used to infer any of a number of compositional properties of the test material. These properties include, but are not restricted to:

moisture content
 salt content
 bulk density
 metal content
 fat content
 protein content In one embodiment of the invention, one or more properties may be measured simultaneously (ie concurrently) or in series by analyzing the received microwave signals accordingly.

Figure 4:
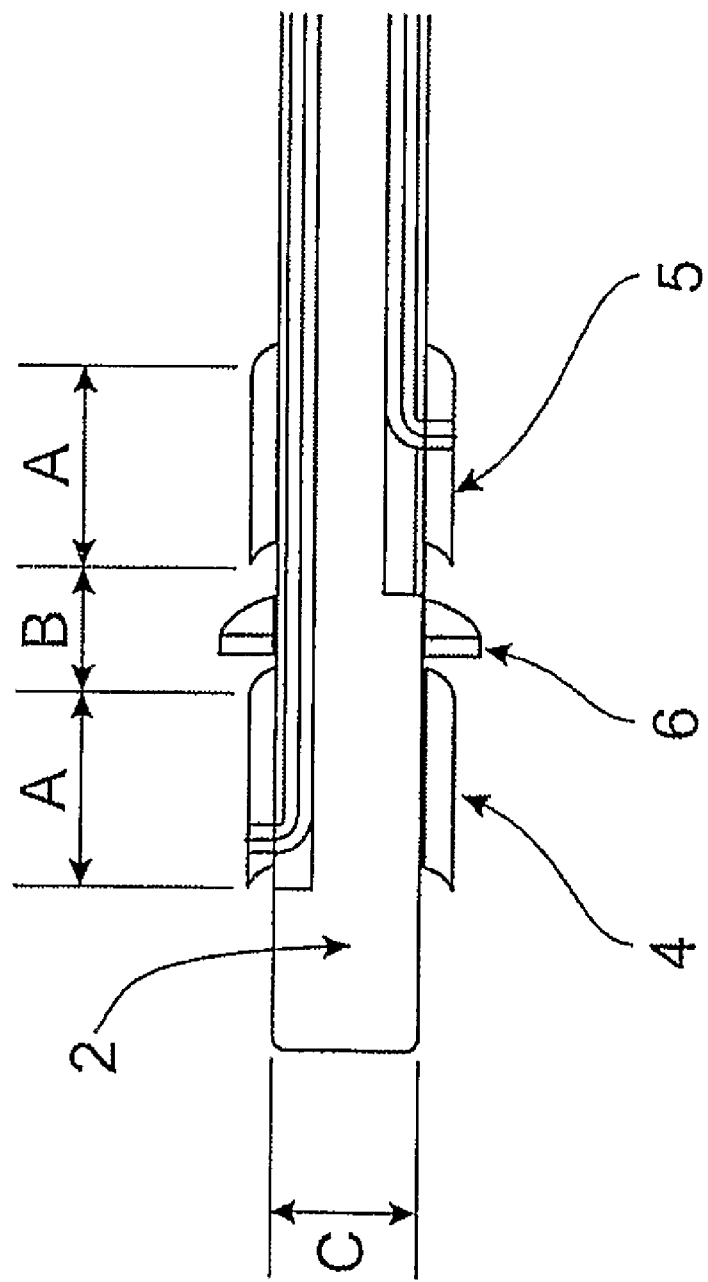
FIG. 4 shows the range of possible dimensions of the probe.

The preferred operating frequency of the antenna configuration may be determined by a set of fundamental dimensions. The fundamental dimensions of one embodiment of the antenna configuration are shown in FIG. 4. The fundamental dimensions of Table 1 allow the system to operate optimally between 0.1 GHz and 20 GHz.

TABLE 1

Fundamental dimension limits

| | Min (mm) | Max (mm) |
|---|---|---|
| A | 2 | 50 |
| B | 2 | 200 |
| C | 2 | 100 |

Figure 5:
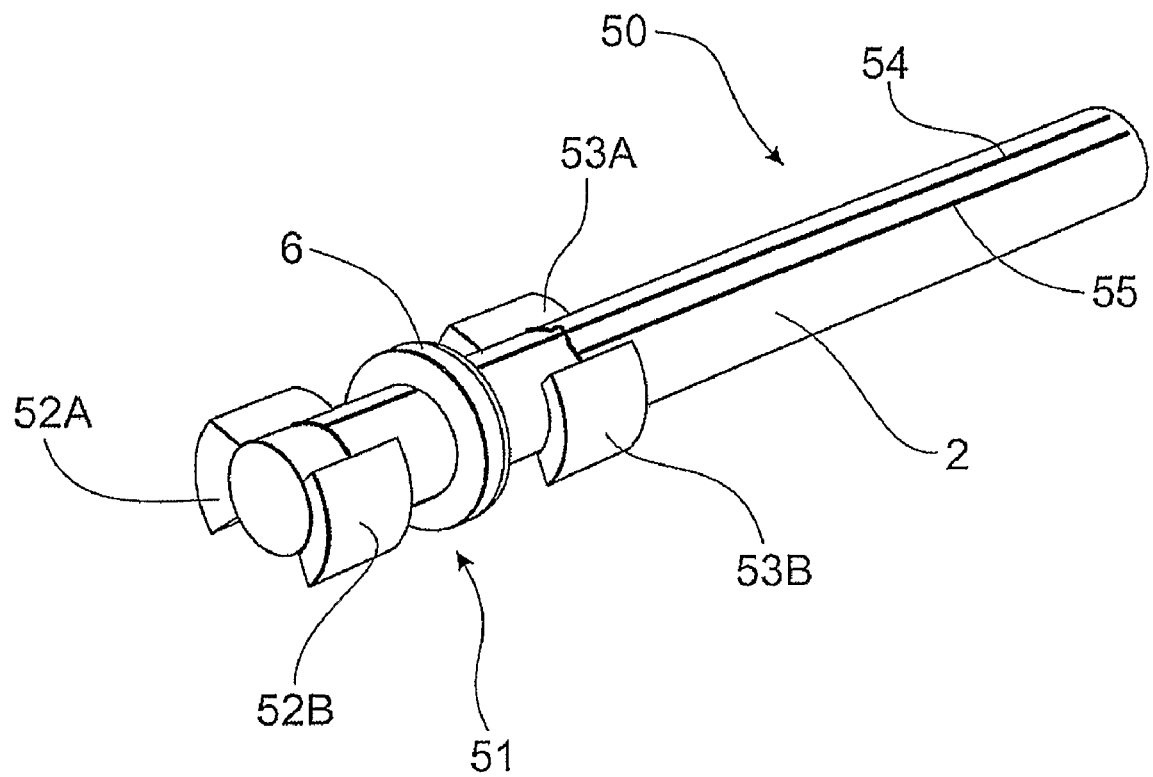
FIG. 5 is a perspective view of a second embodiment of a probe.
Figure 6:
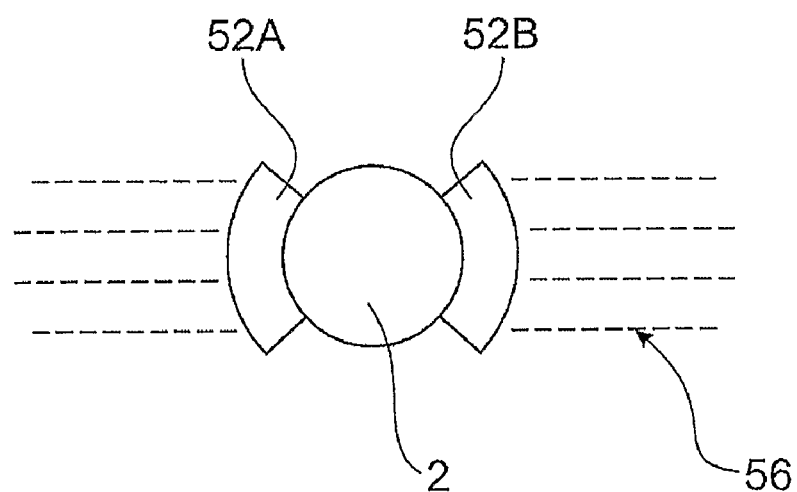
FIG. 6 is an end view of the probe of FIG. 5.

Referring to FIG. 5, there is shown a schematic of a second embodiment of the microwave probe 50 consisting of a support member 2 with an antenna arrangement 51 towards one end. The antenna arrangement 51 comprises a transmit antenna of two brass lobes 52A and 52B and a receive antenna of two brass lobes 53A and 53B. The transmitting antenna lobes are separated from the receiving antenna lobes by a barrier 6, as described above. The geometry of the microwave field generated by the antenna arrangement is linear or part-toroidal as represented by 56 in FIG. 6.

The arrangement, dimensions and shape of the antenna may be varied in order to provide a microwave field geometry that corresponds to the particular sample application. For example, a linear field, rather than toroidal, may be more suited for measurements in a sample with only a shallow depth.

Microwave signals are carried to both parts of the transmitting antenna 52A and 52B by coaxial cable 54 and returned for signal processing from both parts of the receiving antenna 53A and 53B by coaxial cable 55.

Similarly to the first embodiment, if support member 2 is formed from a material capable of conducting microwave signals, insulation material will be required between the support rod and the antennae.

EXAMPLES

Garry: Is There More Recent Data you Wish to Include?

Example 1

The probe of the first embodiment described above has been successfully demonstrated to accurately measure the moisture content in mono-ammonium phosphate (MAP) fertilizer. Standard samples of the MAP fertilizer were created with specific moisture contents, which were independently confirmed. A probe using an embodiment of the antenna design was immersed into the material, and the signal attenuation and phase shift were measured. These measurements were correlated against the moisture content of the samples. The results are presented in Table 2 and FIG. 7.

Figure 7:
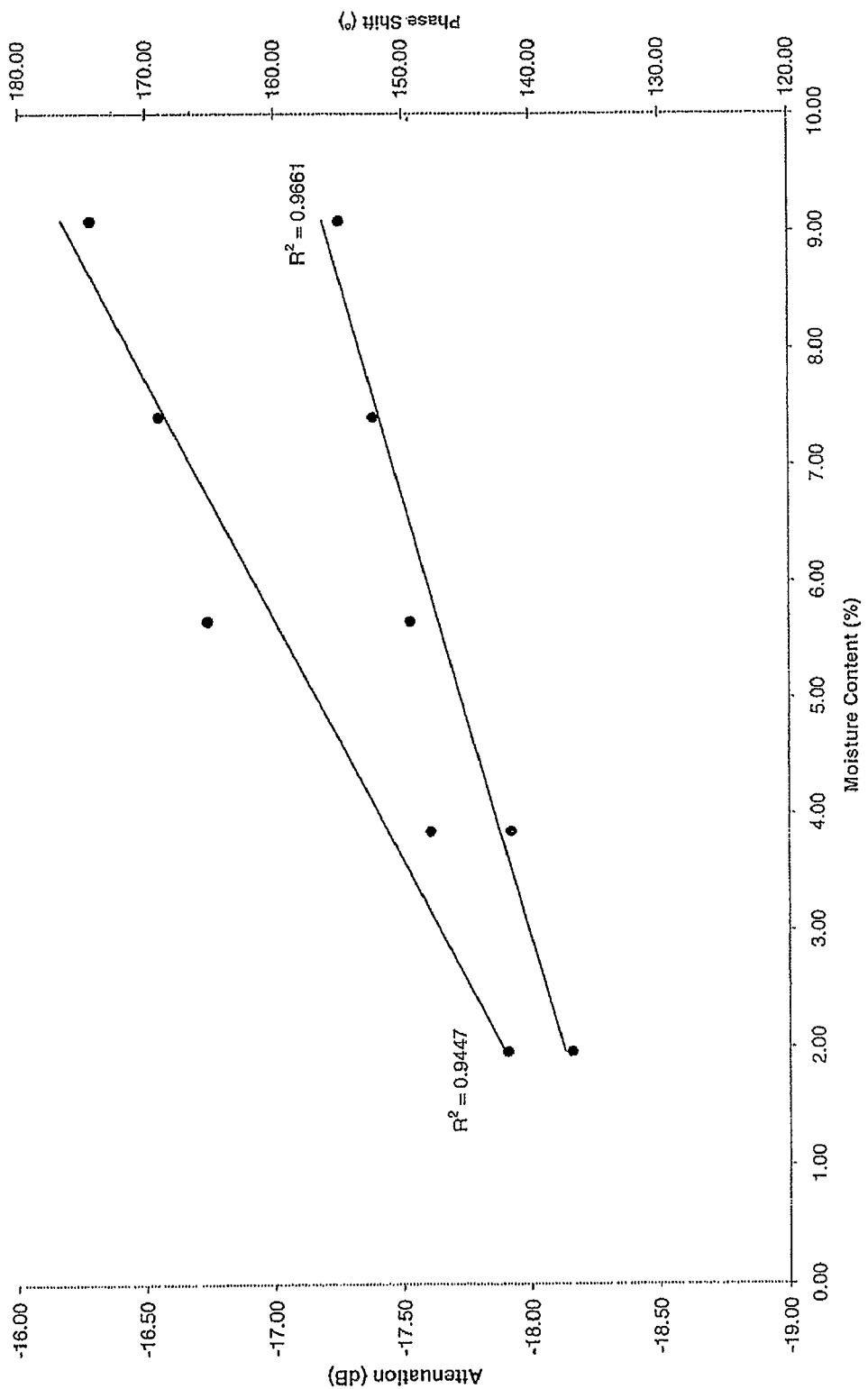
FIG. 7 displays a plot of performance when measuring moisture content.

The tabulated data is plotted in FIG. 7. The coefficient of determination for attenuation $R^2=0.9447$ and for phase shift $R^2=0.9661$. This clearly demonstrates that the probe and associated microwave signal processing can be used to accurately determine moisture content (or other property) of a material.

Throughout the specification the aim has been to describe the preferred embodiments of the invention without limiting the invention to any one embodiment or specific collection of features. It will therefore be appreciated by those of skill in the art that, in light of the instant disclosure, various modifications and changes can be made in the particular embodiments exemplified without departing from the scope of the present invention.

TABLE 2

Signal attenuation and phase shift for MAP at various moisture contents.

| Moisture Content (%) | Attenuation (dB) | Phase Shift (°) |
| --- | --- | --- |
| 0.00 | −18.39 | 132.70 |
| 1.96 | −17.91 | 136.80 |
| 3.85 | −17.61 | 141.50 |
| 5.66 | −16.74 | 149.40 |
| 7.41 | −16.55 | 152.30 |
| 9.09 | −16.28 | 155.00 |
| 0.00 | −18.39 | 132.70 |

The invention claimed is:

1. A probe comprising:
a support member;
a transmit antenna disposed towards an end of the support member;
a receive antenna disposed adjacent the transmit antenna; and
a signal barrier disposed on the support member between the transmit antenna and the receive antenna so as to force signals traveling from the transmit antenna to the receive antenna to propagate through a surrounding region.

2. The probe as claimed in claim 1, wherein the signals traveling from the transmit antenna to the receive antenna are microwave signals.

3. The probe as claimed in claim 2, wherein the microwave signals travel a toroidal path.

4. The probe as claimed in claim 1, wherein the signal barrier is formed from one or more materials that block direct transmission of a signal between the transmit antenna and the receive antenna.

5. The probe as claimed in claim 4, wherein the one or more materials is selected from the group consisting of brass, microwave absorbing rubber, insulating ceramic material and plastic.

6. The probe as claimed in claim 1, wherein the transmit antenna and the receive antenna are configured to operate at a frequency in a range inclusive of 0.1 GHz and 20 GHz.

7. The probe as claimed in claim 1, wherein the support member is a rod.

8. The probe as claimed in claim 7, wherein the rod is formed from a material that conducts microwave signals.

9. The probe as claimed in claim 8, wherein the material that conducts microwave signals is brass.

10. The probe as claimed in claim 8, wherein the rod further comprises an insulating material.

11. The probe as claimed in claim 10, wherein the insulating material is selected from the group consisting of plastic and ceramic.

12. The probe as claimed in claim 7, wherein the rod is formed from a material that does not conduct microwave signals.

13. The probe as claimed in claim 1, wherein the transmit antenna comprises at least two lobes.

14. The probe as claimed in claim 13, wherein the microwave signals travel a linear path.

15. The probe as claimed in claim 13, wherein the microwave signals travel a part-toroidal path.

16. The probe as claimed in claim 1, wherein the receive antenna comprises at least two lobes.

17. A sample analysis device comprising:
a probe including a transmit antenna disposed towards an end of a support member;
a receive antenna disposed adjacent the transmit antenna; and
a signal barrier disposed on the support member between the transmit antenna and the receive antenna so as to force signals traveling from the transmit antenna to the receive antenna to propagate through a surrounding region;
a source of signals connected to the transmit antenna; and
a signal processor connected to the receive antenna.

18. The sample analysis device as claimed in claim 17, wherein the source of signals is a microwave generator.

19. The sample analysis device as claimed in claim 17, wherein the signal processor is a microprocessor.

20. A method of measuring one or more properties in a sample, including the steps of:
(i) forcing signals traveling from a transmit antenna to a receive antenna to propagate through a surrounding region; and
(ii) measuring a modification of the signals traveling from the transmit antenna to the receive antenna,
wherein the modification is a measure of one or more properties of said sample.

21. The method as claimed in claim 20, wherein the step of forcing signals traveling from the transmit antenna to the receive antenna is performed by a signal barrier.

22. The method as claimed in claim 20, wherein the signals traveling from the transmit antenna to the receive antenna are microwave signals.

23. The method as claimed in claim 20, wherein the modification of the signals traveling from the transmit antenna to the receive antenna is attenuation and/or phase shift.

24. The method as claimed in claim 20, wherein the transmit antenna and the receive antenna are configured to operate at a frequency in a range inclusive of 0.1 GHz and 20 GHz.

25. The method as claimed in claim 20, wherein the one or more properties are selected from the group consisting of moisture content, salt content, bulk density, metal content, fat content and protein content.

26. The method as claimed in claim 20, wherein the one or more properties are measured simultaneously or in series.

* * * * *